(12) United States Patent
Lee et al.

(10) Patent No.: US 8,734,844 B2
(45) Date of Patent: May 27, 2014

(54) SOLID PHASE GOLD NANOPARTICLE SYNTHESIS

(75) Inventors: Chia-Hung Lee, Tainan (TW); Wei-Neng Liao, New Taipei (TW); Shih-Hsun Cheng, Kaohsiung (TW); Jen-Kun Chen, Hsinchu (TW); Chung-Shi Yang, Taichung (TW); Leu-Wei Lo, New Taipei (TW); Yeu-Kuang Hwu, Taipei (TW); Fong-Sian Lin, Taichung (TW)

(73) Assignee: National Health Research Institutes, Miaoli County (TW)

( * ) Notice: Subject to any disclaimer, the term of this patent is extended or adjusted under 35 U.S.C. 154(b) by 297 days.

(21) Appl. No.: 13/109,438

(22) Filed: May 17, 2011

(65) Prior Publication Data

US 2012/0130053 A1 May 24, 2012

Related U.S. Application Data

(60) Provisional application No. 61/345,596, filed on May 18, 2010.

(51) Int. Cl.
*A61K 9/14* (2006.01)

(52) U.S. Cl.
USPC ........................................ 424/489; 204/157.4

(58) Field of Classification Search
None
See application file for complete search history.

(56) References Cited

PUBLICATIONS

Wang et al., Adv. Funct. Mater., 2008, 18, 355-361.*
Pol et al., Chem. Mater. 2003, 15, 1111-1118.*
Kandpal et al., Pramana J. Phys., vol. 69, No. 2, Aug. 2007, pp. 277-283.*
Wang et al. (2007) "Structural properties of 'naked' gold nanoparticles formed by synchrotron X-ray irradiation" J. Synchrotron Rad. 14, 477-482.
Wang et al. (2008) Optimizing the size and surface properties of polyethylene glycal (PEG)—gold nanoparticles by intense x-ray irradiation J. Phys. D: Appl. Phys. 41, 195301 (8pp).
Liu et al. (2008) "Enhanced x-ray irradiation-induced cancer cell damage by gold nanoparticles treated by a new synthesis method of polyethylene glycol modification" Nanotechnology 19, 295104 (5pp).

* cited by examiner

*Primary Examiner* — Michael G Hartley
*Assistant Examiner* — Robert Cabral
(74) *Attorney, Agent, or Firm* — Hsiu-Ming Saunders; Intellectual Property Connections, Inc.

(57) ABSTRACT

A method of synthesizing ligand-conjugated gold nanoparticles (AuNPs) is disclosed. The method comprises: a) providing an amine-modified silica particle; b) providing a solution comprising $Au^{+3}$ ions; c) suspending the amine-modified silica particle in the solution comprising $Au^{+3}$ ions; d) allowing the $Au^{3+}$ ions to be adsorbed and/or immobilized onto the surface of the amine-modified silica particle; e) exposing the $Au^{3+}$ ions immobilized onto the surface of the amine-modified silica particle to radiation to obtain bare gold nanoparticles (AuNPs) adsorbed and/or immobilized onto the surface of the amine-modified silica particle, wherein the bare AuNPs are without organic surface modifications; and f) reacting a ligand with the bare AuNPs adsorbed and/or immobilized onto the surface of the amine-modified SiNP and thereby obtain ligand-conjugated gold nanoparticles (AuNPs).

18 Claims, 8 Drawing Sheets

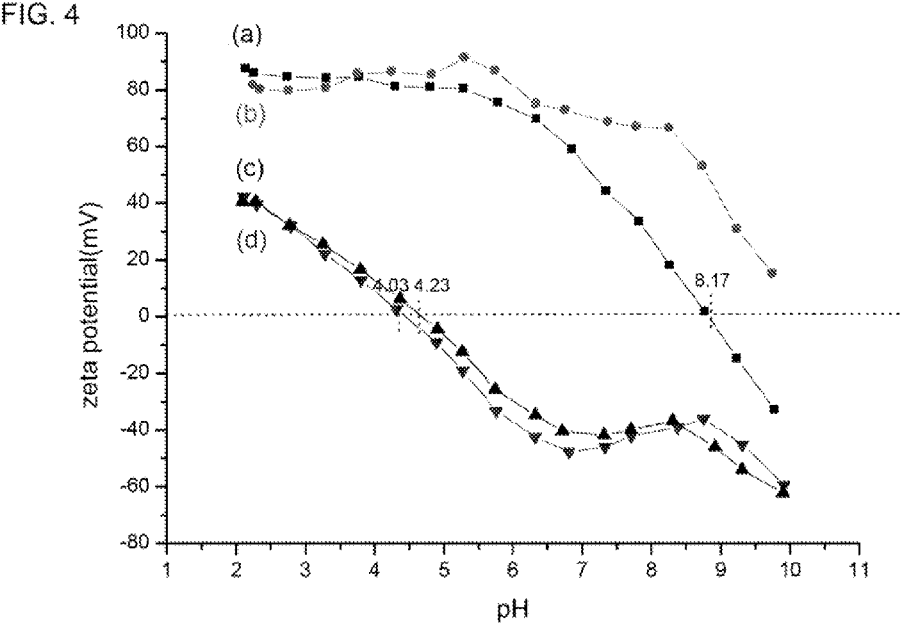
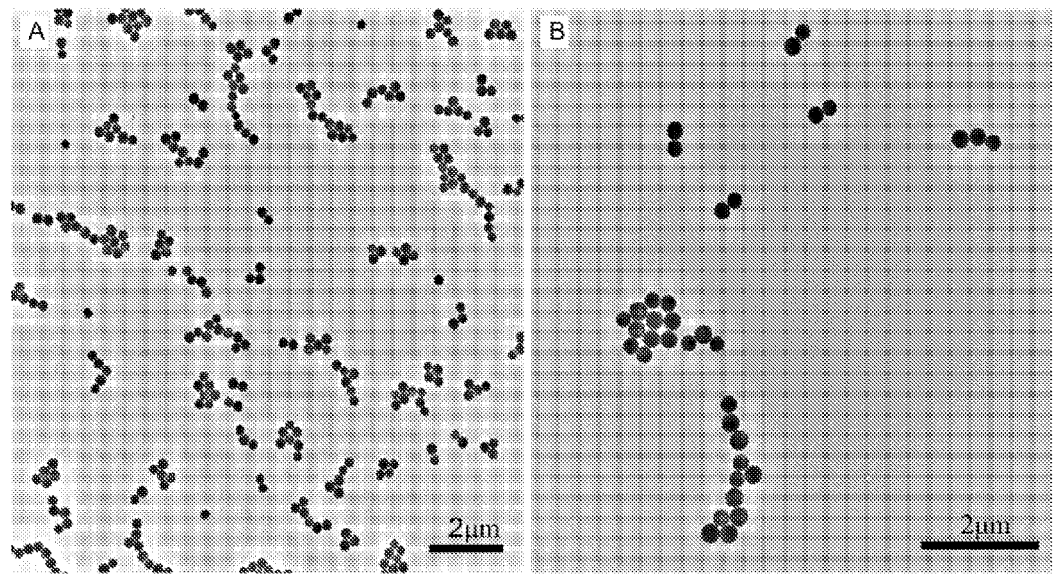
FIG. 5

```
                              SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: TAT

<400> SEQUENCE: 1

Cys Gly Arg Lys Lys Arg Arg Gln Arg Arg Arg
1               5                   10
```

US 8,734,844 B2

SOLID PHASE GOLD NANOPARTICLE SYNTHESIS

REFERENCE TO RELATED APPLICATION

The present application claims the priority to U.S. Provisional Application Ser. No. 61/345,596, filed May 18, 2010, which is herein incorporated by reference in its entirety.

FIELD OF THE INVENTION

The present invention relates generally to gold nanoparticles, and more specifically to solid phase gold nanoparticle synthesis in the absence of a chemical reductant.

BACKGROUND OF THE INVENTION

Recently, an increasing interest was focused on the use of AuNPs for biomedical applications including imaging, sensing, gene delivery, drug delivery, and protein immobilization. Usually, chemical synthesis of AuNPs usually involves the reduction of $Au^{3+}$ ions in the presence of an organic ligand as the stabilizer. Various protection groups such as citrate acid, alkylamine, alkylthiol, cetyltrimethylammonium bromide (CTAB), or polymers must be introduced to mantle the shell of the reduced AuNP surfaces to efficiently prevent the overgrowth and aggregation from the as-synthesized AuNPs. Although AuNPs with reasonable stability and dispersity in solutions can be synthesized with this approach, the post-modification of the AuNP surfaces through ligand exchange usually shows low efficiency and is a time-consuming process since the tight formation of the protective ligands may affect the substitution rate of the exchanged ligands.

More recently, a solution phase synthesis of PEG-protected AuNPs by using synchrotron X-ray as a reduction source has been developed. However, the solution-phase synthesis of AuNPs through a high energy bombardment of the $Au^{3+}$/PEG-polymer precursor under synchrotron X-ray usually produces a complicated free radical reaction and caused a serious cross-linkage and tangle of the polymerization-PEG outside the shell of AuNPs. Due to the formation of a covalently reticular structure of the PEG chains in the surface of AuNPs, further post-modifications of AuNP surfaces through a ligand exchange are very difficult and not feasible. Moreover, the process of solution phase synthesis of AuNPs through reduction from high energy is usually chemically uncontrollable. It produces unwanted chemical residues from $Au^{3+}$ ions and the stabilizer, which makes further purification of AuNPs a difficult task.

Therefore, a heretofore unaddressed need exists in the art to address the aforementioned deficiencies and inadequacies related to gold nanoparticle synthesis, especially in connection with chemical reductant (i.e., reducing agent)-free gold nanogold particle synthesis.

SUMMARY OF THE INVENTION

In one aspect, the invention relates to a method of synthesizing ligand-conjugated gold nanoparticles (AuNPs) comprising:
  providing an amine-modified silica particle;
  providing a solution comprising $Au^{+3}$ ions;
  suspending the amine-modified silica particle in the solution comprising $Au^{+3}$ ions;
  allowing the $Au^{3+}$ ions to be adsorbed and/or immobilized onto the surface of the amine-modified silica particle, wherein the solution has no mesoporous silica nanoparticles (MSN) present;
  exposing the $Au^{3+}$ ions immobilized onto the surface of the amine-modified silica particle to radiation to obtain bare gold nanoparticles (AuNPs) adsorbed and/or immobilized onto the surface of the amine-modified silica particle, wherein the bare AuNPs are without organic surface modifications; and
  reacting a ligand and the bare AuNPs adsorbed and/or immobilized onto the surface of the amine-modified silica particle and thereby obtain ligand-conjugated gold nanoparticles (AuNPs).

In another aspect, the invention relates to a method of synthesizing ligand-conjugated gold nanoparticles (AuNPs) comprising:
  providing a solution comprising an amine-modified silica particle with bare gold nanoparticles (AuNPs) adsorbed and/or immobilized onto the surface thereof, wherein the bare AuNPs are without organic surface modifications and the solution has no mesoporous silica nanoparticles (MSN) present; and
  reacting a ligand and the AuNPs adsorbed and/or immobilized onto the surface of the amine-modified silica particle and thereby obtain ligand-conjugated AuNPs.

Further in another aspect, the invention relates to a composition comprising ligand-conjugated AuNPs synthesized according to a method mentioned above, in which the ligand-conjugated AuNPs have a ligand surface density of greater than 16, 15, 14, 13, 12, 11, 10, 9, 8, 7, 6, 5, 4, 3 or 2 ligand molecules/$nm^2$, and/or comprise greater than 80%, 70%, 60%, 50%, 40%, 30% or 25% of the ligand by weight.

Yet in another aspect, the invention relates to a composition comprising ligand-conjugated AuNPs synthesized according to a method described above.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 4 shows Zeta potential of (a) $SiO_2$-1N particle template; (b) $SiO_2$-3N particle template, (c) $SiO_2$-1N-AuNPs, and (d) $SiO_2$-3N-AuNPs at different titration pHs. The pH values of PZC (point of zero charge) of $SiO_2$-1N particle template, $SiO_2$-1N-AuNPs, and $SiO_2$-3N-AuNPs were 8.17, 4.23 and 4.03, respectively.

FIG. 5 shows TEM images of (A) $SiO_2$-1N and (B) $SiO_2$-3N nanoparticle samples.

DETAILED DESCRIPTION OF THE INVENTION

Definitions

Figure 1:
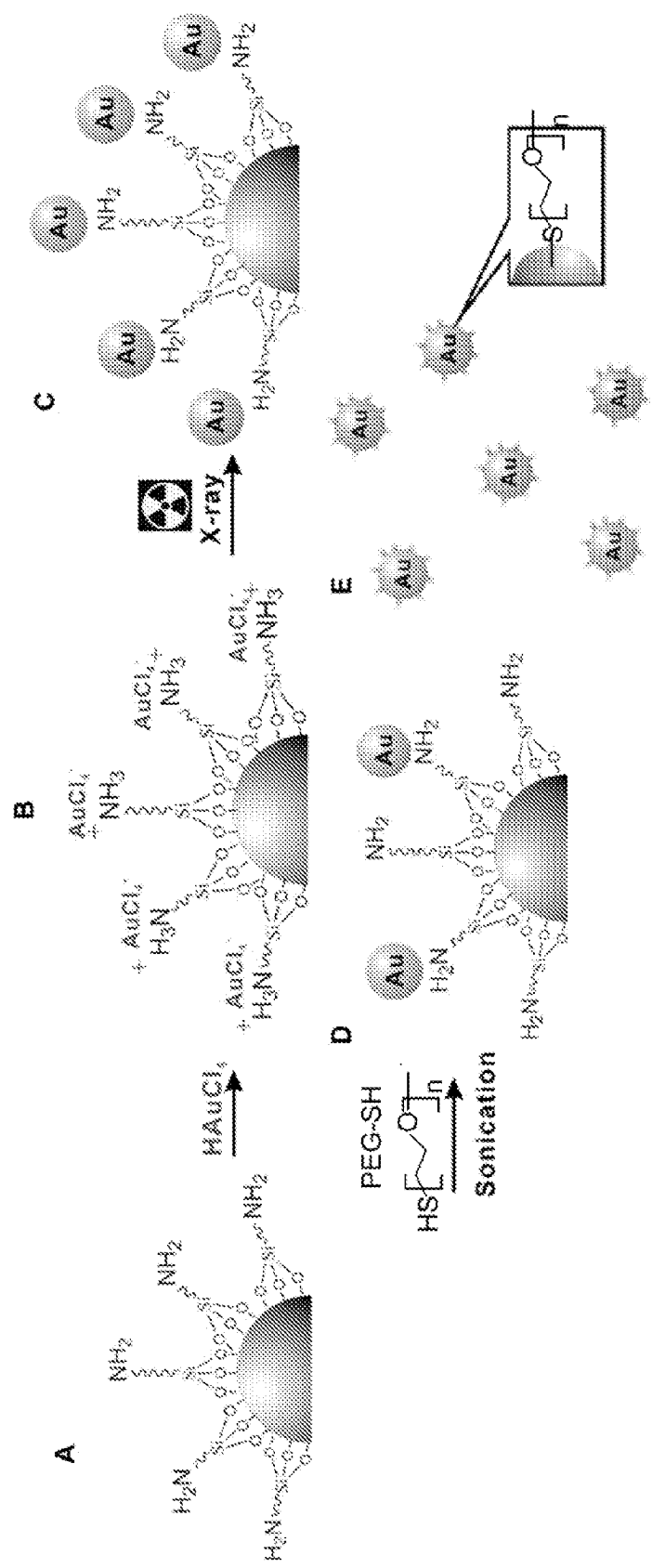
FIG. 1A is a schematic representation of an amine-modified silica nanoparticle (SiNP).
FIG. 1B shows $Au^{3+}$ ions adsorbed onto the amine-modified SiNP surface.
FIG. 1C shows gold nanoparticles are synthesized on the amine-modified SiNP surface after X-ray irradiation of $Au^{3+}$ ions.
FIG. 1D shows the amine-modified SiNP template with residual AuNPs remaining adsorbed on the surface of the particle after removal of AuNPs by PEG ligand exchange.
FIG. 1E shows $PEG_{5000}$-modified AuNPs removed from the amine-modified SiNP template.
FIG. 1F shows a TEM image of amine-modified silica nanoparticles.
FIG. 1G shows a TEM image of gold nanoparticles synthesized on the amine-modified SiNP surface after X-ray irradiation of $Au^{3+}$ ions adsorbed onto the amine-modified SiNP surface of FIG. 1B.
FIG. 1H shows a TEM image of the amine-modified SiNP template after removal of AuNPs by PEG ligand exchange.
FIG. 1I shows a TEM image of PEG-conjugated AuNPs of FIG. 1E.
Figure 1:
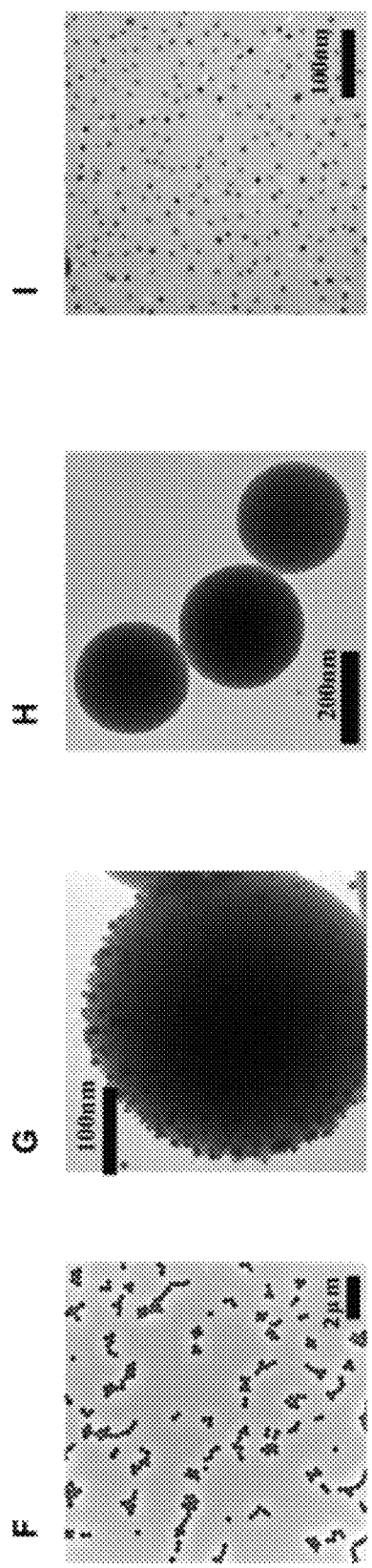

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, when a number or a range is recited, ordinary skill in the art understand it intends to encompass an appropriate, reasonable range for the particular field related to the invention.

The term "radiation" is a process in which energetic particles or energy or waves travel through a medium or space.

The terms "naked gold nanoparticle" and "bare gold nanoparticle" are interchangeable, and shall generally mean a gold nanoparticle without organic surface modifications.

An amine-modified silica nanoparticle (SiNP) shall generally mean a silica nanoparticle with surface modified with one or more than one amine group. An amine contains a basic nitrogen atom with a lone pair.

The terms "ligand-modified AuNPs" and "ligand-conjugated AuNPs" are interchangeable.

The term "silica-1N-AuNP" shall generally mean a complex made of gold nanoparticles absorbed and/or immobilized an amine-modified silica nanoparticle (SiNP), in which the surface of the SiNP is modified with a monoamine functional group (e.g., an aminopropyl functional group).

The term "silica-3N-AuNP" shall generally mean a complex made of gold nanoparticles absorbed and/or immobilized an amine-modified silica nanoparticle (SiNP), in which the surface of the SiNP is modified with a triamine functional group (e.g., a diethylenetriamine functional group).

The term "biopolymers" shall generally mean polymers produced by living organisms. Biopolymers contain monomeric units that are covalently bonded to form larger structures. For example, polynucleotides are composed of nucleotide monomers; polypeptides are composed of amino acids and polysaccharides are often linear bonded polymeric carbohydrate structures.

As used herein, the term "sonication" shall generally mean the act of applying sound (usually ultrasound) energy to agitate particles in a sample.

The term "ligand surface density" shall generally mean the density of a ligand conjugated onto the surface of a nanoparticle and is expressed as ligands/$nm^2$ or ligand molecules/$nm^2$, that is, the number of ligand molecules per square nanometer area of a nanoparticle.

The method of synthesizing ligand-conjugated AuNPs according to the invention does not involve a mesoporous silica nanoparticle (MSN) either in the process of synthesizing bare AuNPs or in the process of synthesizing ligand-conjugated AuNPs.

In one aspect, the invention relates to a method of synthesizing ligand-conjugated gold nanoparticles (AuNPs) comprising:
    providing an amine-modified silica particle;
    providing a solution comprising $Au^{+3}$ ions;
    suspending the amine-modified silica particle in the solution comprising $Au^{+3}$ ions;

allowing the Au$^{3+}$ ions in the solution to be adsorbed and/or immobilized onto the surface of the amine-modified silica particle; wherein the solution has no mesoporous silica nanoparticles (MSN) present;

exposing the Au$^{3+}$ ions immobilized onto the surface of the amine-modified SiNP to radiation to obtain bare gold nanoparticles (AuNPs) adsorbed and/or immobilized onto the surface of the amine-modified silica particle, wherein the bare AuNPs are without organic surface modifications; and reacting a ligand with the bare AuNPs adsorbed and/or immobilized onto the surface of the amine-modified silica particle to obtain ligand-conjugated gold nanoparticles (AuNPs), wherein the ligand comprises a thiol group.

In one embodiment of the invention, the amine-modified silica particle is at least one chosen from monoamine-modified silica particle, diamine-modified silica particle and triamine-modified silica particle.

In another embodiment of the invention, the weight ratio of the ligand-conjugated AuNPs versus the AuNPs adsorbed and/or immobilized onto the surface of the amine-modified silica particle is greater than 80%, 70%, 60%, 50% or 40%.

In another embodiment of the invention, the ligand-conjugated AuNPs comprise greater than 80%, 70%, 60%, 50%, 40%, 30% or 25% of the ligand by weight.

In another embodiment of the invention, the ligand-conjugated AuNPs have a ligand surface density of greater than 16, 15, 14, 13, 12, 11, 10, 9, 8, 7, 6, 5, 4, 3 or 2 ligand molecules/nm$^2$.

In another embodiment of the invention, the ligand comprises at least one polymer chosen from a synthetic polymer and a biopolymer.

In another embodiment of the invention, the ligand is at least one chosen from polyethylene glycol (PEG), PEG derivatives, TAT and glutathione (GSH), a polynucleotide and a protein.

In another embodiment of the invention, the radiation is chosen from X-rays, microwaves, gamma-rays and neutrons.

In another embodiment of the invention, the Au$^{3+}$ ions immobilized onto the surface of the amine-modified silica particle are exposed to synchrotron X-ray.

In another embodiment of the invention, the method as aforementioned further comprises: removing the amine-modified silica particle by centrifugation and obtain a supernatant comprising the ligand-conjugated AuNPs; and centrifuging the supernatant to collect the ligand-conjugated AuNPs.

In another embodiment of the invention, the ligand-reacting step is performed at a pH of greater than or equal to 8.0, 8.5 or 9.0.

In another embodiment of the invention, the ligand-reacting step is performed at a pH of greater than 6.0.

In another embodiment of the invention, the ligand-reacting step is performed under a condition that permits the ligand to carry a negative charge Further in another embodiment of the invention, the ligand-reacting step is performed under sonication.

Yet in another embodiment of the invention, the radiation-exposing step is performed in the absence of an organic ligand and the ligand-reacting step is performed in the absence of a chemical catalyst.

In another aspect, the invention relates to a method of synthesizing ligand-conjugated gold nanoparticles (AuNPs) comprising:

providing a solution comprising an amine-modified silica particle with bare gold nanoparticles (AuNPs) adsorbed and/or immobilized onto the surface thereof, wherein the bare AuNPs are without organic surface modifications and the solution has no mesoporous silica nanoparticles (MSN) present; and reacting a ligand and the AuNPs adsorbed and/or immobilized onto the surface of the amine-modified SiNP to obtain ligand-conjugated AuNPs, wherein the ligand comprises a thiol group.

Further in another aspect, the invention relates to a composition comprising ligand-conjugated AuNPs synthesized according to a method mentioned above, in which the ligand-conjugated AuNPs have a ligand surface density of greater than 16, 15, 14, 13, 12, 11, 10, 9, 8, 7, 6, 5, 4, 3 or 2 ligand molecules/nm$^2$, and/or the ligand is greater than 80%, 70%, 60%, 50%, 40%, 30% or 25% of the ligand-conjugated AuNPs by weight.

Yet in another aspect, the invention relates to a composition comprising ligand-conjugated AuNPs synthesized according to a method described above.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

The invention relates to a rapid and high-yield method for modification of AuNP surfaces with an expectant organo-thiol ligand such as thiol-PEG. The combination of solid phase synthesis and synchrotron X-ray allows synthesis of naked AuNPs which have strong affinity to desired modifying ligands and therefore modification of AuNP surfaces becomes simple, efficient and fast.

The invention relates to a method of synthesizing AuNPs using a synchrotron X-ray and a hard silica template-based synthetic approach. This green chemical method, which takes advantages of intense X-ray reductive power, rather than using a reducing agent, and a solid phase template, instead of a soluble stabilizing agent, can produce a uniform size of naked AuNPs suitable for rapid post-modifications with expectative organic ligands through a strong affinity. Thus, it is feasible to efficiently increase the stability and modification efficiency of AuNPs, and at the same time greatly decrease Au$^{3+}$ toxicity and save time by avoiding complicate steps of ion-exchange and purification. The synthetic pathway may be summarized as follows: (1) catching Au$^{3+}$ ions onto a hard silica template, (2) producing reduced naked AuNPs on the solid surfaces of the template by employing synchrotron X-ray radiation, and (3) releasing the naked AuNPs from the hard template through in situ surface modifications of the naked AuNPs by adding an organo-thiol ligand and produce organo-modified AuNPs.

The radiation that were employed for reducing Au$^{3+}$ to produce bare AuNPs includes, but not limited to, X-rays (12.5 eV), microwaves (120° C.), gamma-rays (Co$^{60}$) and neutrons (2 Gy/hr, neutrons: 3.4×10$^{12}$ n·cm$^{-2}$·sec$^{-1}$ (0.025 eV).

Materials.

Tetraethoxysilane (TEOS), ethanol, ammonium hydroxide (30%), 3-aminopropyltrimethoxysilane (APTMS), N-[3-(trimethoxylsiliyl)-propyl]diethylene-triamine, and Gold(III) chloride were purchased from Acros. Poly(ethylene glycol)

thiol (MW=5000) were purchased from NANOCS. Glutathione (GSH) was purchased from SIGMA-ALDRICH® and TAT (CGRKKRRQRRR; SEQ ID NO: 1) from AnaSpec Inc.

Preparation of Bare Silica Nanoparticles.

The bare silica nanoparticles (SiNP) were synthesized through a modified Stöber procedure. Briefly, a mixture of 2.0 mL of ammonia (30%), 6.3 mL of Milli-Q dd$H_2O$, 2.23 mL of TEOS, and 49.5 mL of ethanol (99.5% v/v as solvent) was stirred at room temperature for 20 hrs. Samples were collected by centrifugation at 11000 rpm for 20 min, washed, and redispersed in ethanol for three times. The SiNP differs from mesoporous silica nanoparticle (MSN).

Amine Post-Modification of Amine-Modified Silica Nanoparticles.

The synthetic condition of 3-aminopropyltrimethoxysilane- or N-[3-(trimethoxylsiliyl)-propyl]diethylene-triamine-modified silica nanoparticles was prepared as follows. The collected silica nanoparticles were first dispersed in 100 mL EtOH. Then, 2 mL of aminosilanes were added into the silica-EtOH solution under stirring. The reaction was carried out at 70° C. for 20 h. The modified nanoparticles were collected by centrifugation at 11000 rpm for 20 min, washed, and redispersed with ethanol for three times.

Synthesis of Naked Gold Nanoparticles on Silica Templates.

The adsorption of $Au^{3+}$ ions onto the surfaces of aminosilane-modified silica nanoparticles can be achieved by electrostatic attractions between positively charged surfaces of amine-modified silica and negative charge of $AuCl_4^-$ ions. The strong attractions within the ion pair —$NH_3^+$ and $AuCl_4^-$ provided stability for further reducing reaction to synthesize naked AuNPs onto the surfaces of silica nanoparticle templates. Different loading percentages of $HAuCl_4$ onto silica nanoparticle templates (10, 20, 30, 40 and 50% of weight percentages to silica nanoparticles) have been studied by adding different amounts of $HAuCl_4$ (stock solution: 100 mg $HAuCl_4$ in 1 mL $H_2O$) aqueous solution into 50 mg of aminosilane-modified silica nanoparticles. The mixture was stirred at room temperature for 6 h. The produced Silica NPs-$NH_3^+$ $AuCl_4^-$ complexes were washed with pure water twice, centrifuged at 11000 rpm for 20 min. The reduction of Silica NPs-$NH_3^+$ $AuCl_4^-$ complexes were performed by re-suspending the above Silica NPs-$NH_3^+$ $AuCl_4^-$ complexes with 5 mL $H_2O$ and then the solution was exposed to hard X-rays (12.5 Kev for about 5 min) from the BL01A beamline of NSRRC (National Synchrotron Radiation Research Center, Hsinchu, Taiwan). A slit was used to obtain a transversal beam section of 13 mm×9 mm, which matched the dimensions of the tubes. The exposure time was 5 min. Detailed descriptions of the experimental system were as previously reported.

Synthesis of $PEG_{5000}$-Modified AuNPs by Using Solid Phase Approach.

After synchrotron irradiation of the amine-modified silica NPs-$NH_3^+$ $AuCl_4^-$ samples, 350 μL, of $PEG_{5000}$-SH of various concentrations (0, 0.47, 0.9, 1.78, 3.6, 5 mM) were added to 100 μL of the reductive samples (2.89 mg of Silica-1N (3N)-AuNPs). The mixtures were reacted at various pH values from 2 to 9. To remove the PEG-modified AuNPs from the silica template surfaces, sonication of the above mixture was performed for 15 mins. The solid silica nanoparticle template was pelleted by centrifugation at 4000 rpm. The $PEG_{5000}$-modified AuNPs in the supernatant was washed with dd$H_2O$ and centrifuged (13000 rpm for 15 mins) for three times. The pelleted solids of AuNPs-$PEG_{5000}$ samples were freeze-dried for further analysis of FT-IR and TGA.

Characterization.

The ζ-potentials of all the samples were measured with a Malvern Zetasizer 3000 NANOZS. Zeta potential distribution was obtained by averaging ten measurements. The samples were prepared at the concentration of 1 mg in 10 mL of dd$H_2O$. Different pH values were adjusted by HCl or NaOH (0.02 M). The morphology of the samples was characterized with TEM (Hitachi, H-7650 operating at an acceleration voltage of 80 kV). FT-IR spectra were recorded on a Nicolet 550 spectrometer using a KBr pellet. About 1 mg of sample was mixed with dried KBr (300 mg) and then pressed. UV-Vis spectra were taken on a Hitachi U-3010 spectrophotometer. The spectra were measured within the wavelength range of 400 to 800 nm against a standard. Thermogravimetric analysis (TGA) data were obtained with a NETZCH TG209-F3 thermogravimetric analyzer. Samples were heated from 30 to 650° C. at a heating rate of 15° C. per minute under nitrogen. The Au content of the samples was measured by inductively coupled plasma mass spectrometer (ICP-MS). Sample preparation was as follows: 100 μL of Silica-1N(3N)-AuNPs samples were put into TFM digestion vessel. Then adding a mixture of 0.5 mL of $HNO_3$ and 1.5 mL of HCl into the sample. The sample was heated at 200° C. through a microwave machine for 20 min, transferred to PP vials and diluted 200 times.

Results

FIG. 1 illustrates the solid phase synthesis of PEG-modified AuNPs. Firstly, $AuCl_4^-$ anions (FIG. 1B) were absorbed onto the surfaces of the hard template 3-aminopropyl-trimethoxysilane- or $N^1$-[3-(trimethoxysilyl)-propyl]diethylenetriamine-modified SiNPs (FIG. 1A) through electrostatic attraction (FIG. 1B). The zeta potentials for all the amino-modified silica NPs were as high as +60 mV in the pH range of 2-7 (FIG. 4). Large amounts of $AuCl_4^-$ ions could be easily adsorbed onto the hard template amine-modified silica nanoparticles (FIG. 1B). Then, $Au^{3+}$ ions on the surface of the silica template were irradiated by synchrotron X-Ray for 5 minutes. After the irradiation, AuNPs were produced from the reduction of $Au^{3+}$ (FIG. 1C). These AuNPs appeared to be of uniform size and highly dispersed on the surface of the silica template according to TEM images. In comparison with chemical approaches, which usually use a reducing reagent to produce AuNPs, synchrotron X-ray irradiation provided a rapid and clean approach to the synthesis of naked AuNPs on a hard template surface (FIG. 1C) without using chemical reduction reagents and stabilizers. The naked AuNP surface allowed rapid and easy conjugation of functional groups via thiol-containing ligands. Thus, $PEG_{5000}$-SH can be used to remove AuNPs from the amine-modified silica template through a ligand exchange reaction, which is a one-step approach to desorbtion and modification of AuNPs in situ (FIG. 1D-E). Owing to the high affinity between the bare AuNPs and the thiol group, the AuNP surface modification by thiol. PEG was highly efficient and could be achieved by a short period of sonication of the mixture of amine-modified silica-AuNPs and $PEG_{5000}$-SH in dd$H_2O$. As illustrated here, the size of the $SiO_2$ template is 250 nm, and the size of the AuNPs that were generated and adsorbed/immobilized on the SiO2 template was less than 100 nm.

Figure 2:
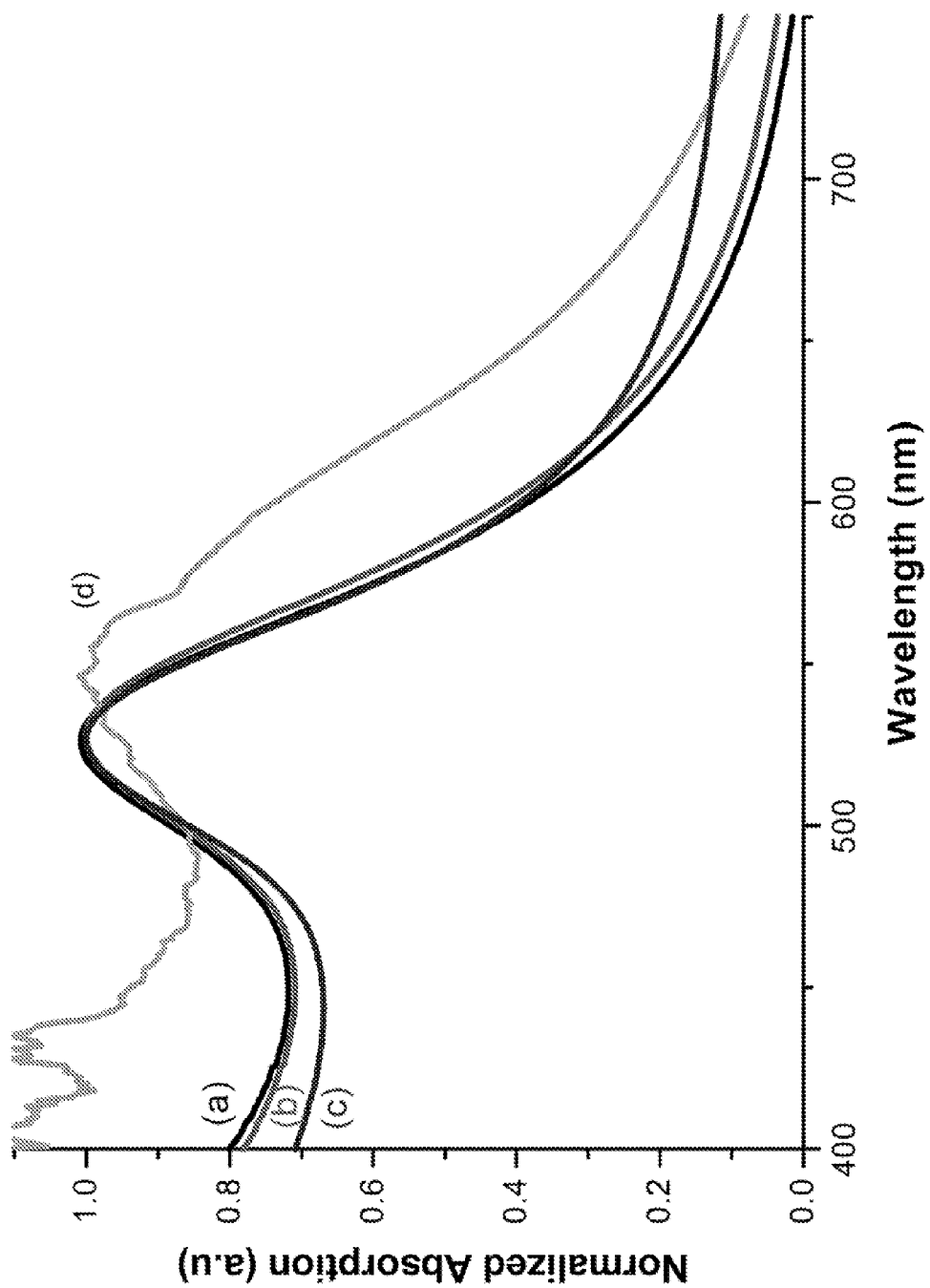
FIG. 2 shows UV-Vis spectra of AuNPs removed from (a) $SiO_2$-1N-AuNPs samples, or (b) $SiO_2$-3N-AuNPs samples by adding 3.6 mM $PEG_{5000}$-SH. (c) $SiO_2$-1N-AuNPs samples were pre-treated with 3.6 mM $PEG_{5000}$-SH at pH 7.0 and then the silica template was dissolved by 0.1% $NH_4F$ buffer. (d) In the absent $PEG_{5000}$-SH, naked AuNPs were removed from $SiO_2$-1N-AuNPs samples by dissolution of silica template in 0.1% $NH_4F$ buffer.
Figure 10:
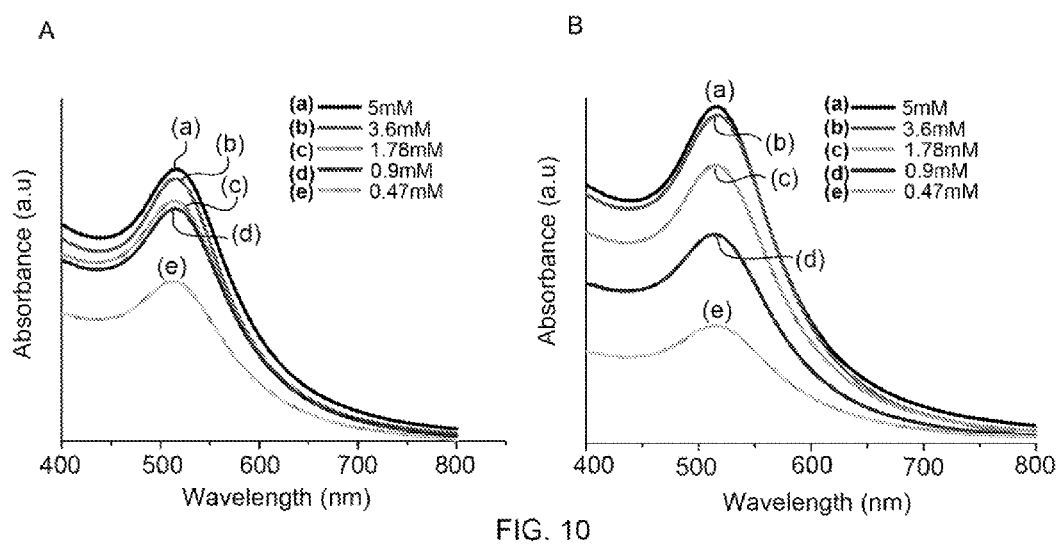
FIG. 10 shows UV-Vis spectra of PEG-conjugated AuNPs removed from (A) $SiO_2$-1N-AuNPs, and (B) $SiO_2$-3N-AuNPs, respectively, with various concentrations of the ligand $PEG_{5000}$-SH (5, 3.5, 1.78, 0.9, and 0.47 mM).

In order to optimize the yield of $PEG_{5000}$-SH modified AuNPs (FIG. 1E), ligand exchange reactions were conducted at various concentrations of $PEG_{5000}$-SH (0.47, 0.9, 1.78, 3.6, and 5 mM) and different pH values (pH 2-9). The results of UV-Vis spectra indicated that an efficient replacement and modification occurred under the condition of 3.6 mM of $PEG_{5000}$-SH and pH 9.0 (FIG. 10). After the release of $PEG_{5000}$-modified AuNPs from the amine-modified silica template surface, the solid template could be easily separated and removed by centrifugation at 4000 rpm for 15 mins. The PEG-stabilized AuNPs remained in the solution phase. According to the TEM image studies, PEG-conjugated AuNPs appeared to have uniform size of about 10 nm (FIG. 1I). The PEG$_{5000}$-SH-replaced AuNPs from either SiO$_2$-1N or -3N at pH=9 and 3.6 mM PEG$_{5000}$-SH were well dispersed in the buffer. There were no aggregations being observed, which would have been reflected from the shift of SPR peak and the color changes in the solution phase (FIG. 2, curves (a) and (b)). To verify that naked AuNPs existed on the amine-modified silica-solid surfaces, the silica template of Silica-1N-AuNPs samples was etched by using 0.1% (v/v) NH$_4$F buffer at pH 7.0. After removing the silica template of the Silica-1N-AuNPs samples in the absence of the stabilizer PEG$_{5000}$-SH, the naked AuNPs became seriously aggregated and produced precipitation. The UV-Vis spectra, therefore, showed a right-shift of the SPR band to 550 nm (FIG. 2, curve (d)).

A comparative experiment was performed by pre-treating PEG$_{5000}$-SH (3.6 mM) with Silica-1N-AuNPs samples at pH 7.0. The producted Silica-1N-AuNPs-PEG$_{5000}$ solids were centrifuged and then the silica template was further dissolved under the same condition as aforementioned. It was observed that AuNPs produced from the pre-treated PEG$_{5000}$-SH samples showed a very high stability in 0.1% (v/v) NH$_4$F buffer at pH 7.0. This clearly proved that the serious aggregation of AuNPs in the template-removed Silica-1N-AuNPs samples was mainly due to the naked surfaces, which showed very high reactivity and un-stability when they were removed from the solid surface of the amine-modified silica template.

Figure 3A:
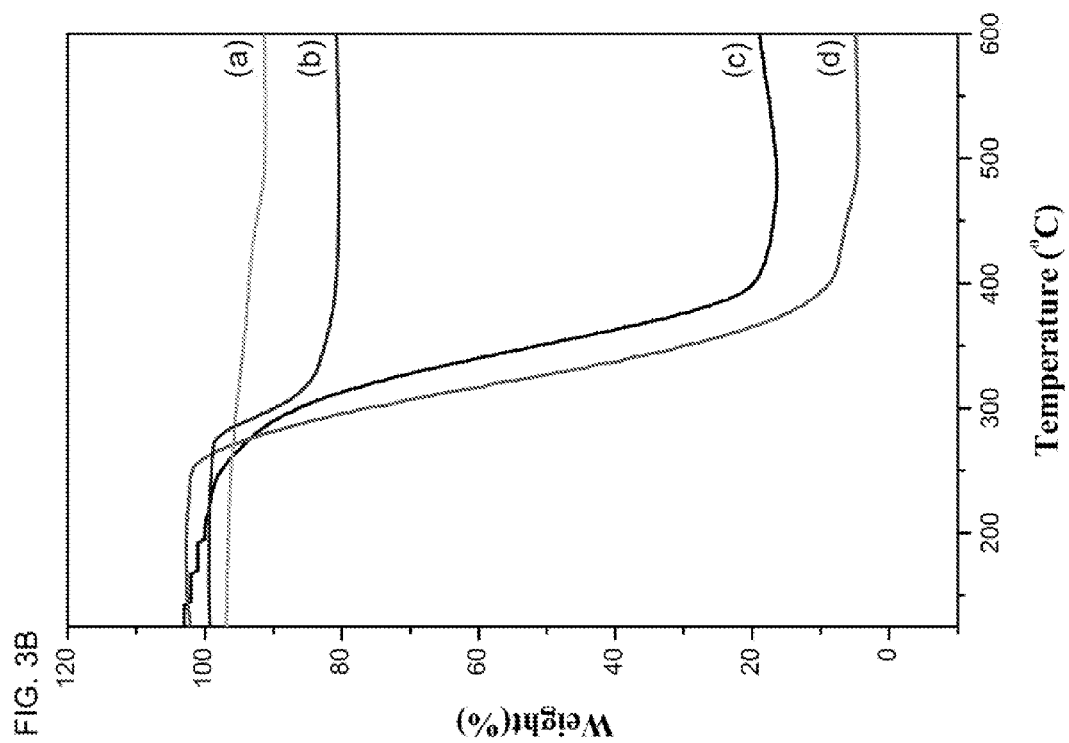
FIG. 3A shows FTIR spectra of PEG5000-conjugated AuNPs synthesized from reacting PEG with $SiO_2$-1N-AuNPs (a) or with $SiO_2$-3N-AuNPs (b).
Figure 3B:
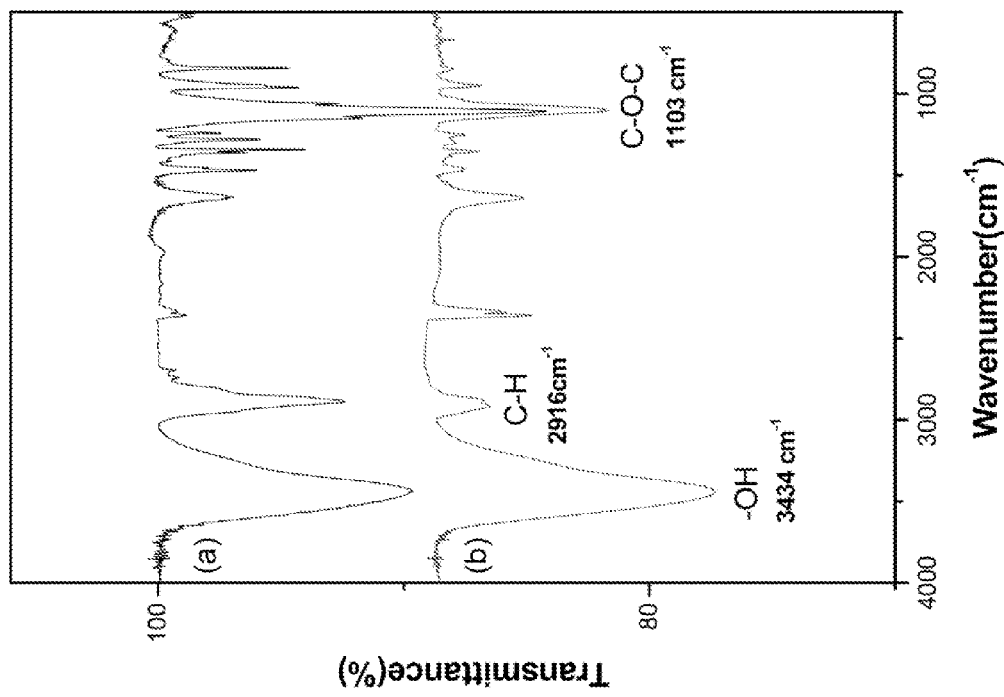
FIG. 3B shows TGA of (a) naked AuNPs, (b) PEG-conjugated AuNPs synthesized by PEG post-modification of citrate-reduced/protected AuNPs, (c) PEG-conjugated AuNPs synthesized by reacting PEG with silica-1N-AuNPs, and (d) PEG-conjugated AuNPs synthesized by reacting PEG with silica-3N-AuNPs.
Figure 6:
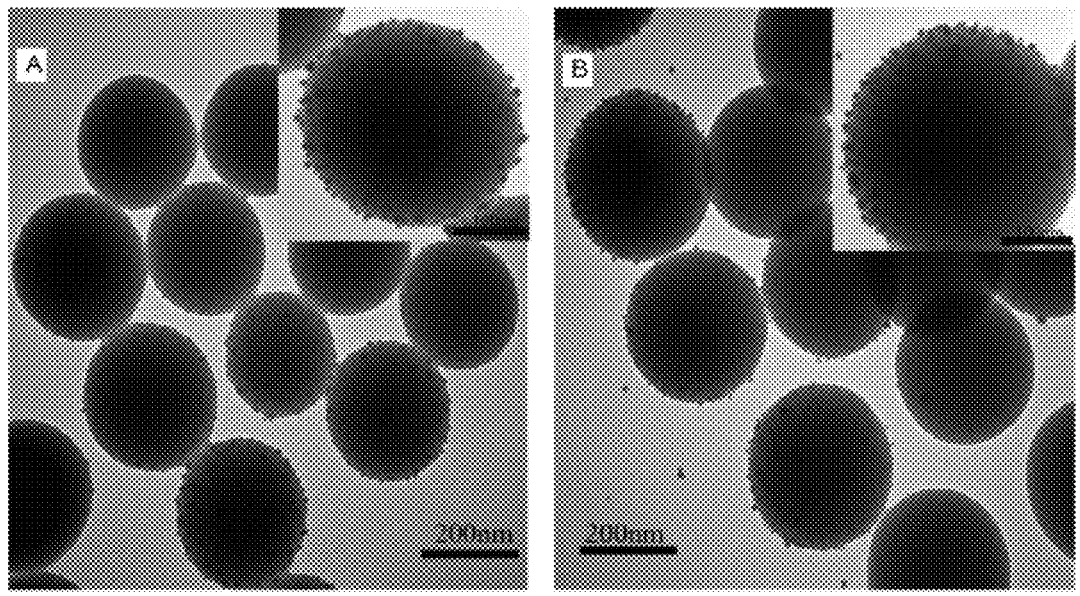
FIG. 6 shows TEM images of (A) $SiO_2$-1N-AuNPs and (B) $SiO_2$-3N-AuNPs.
Figure 7:
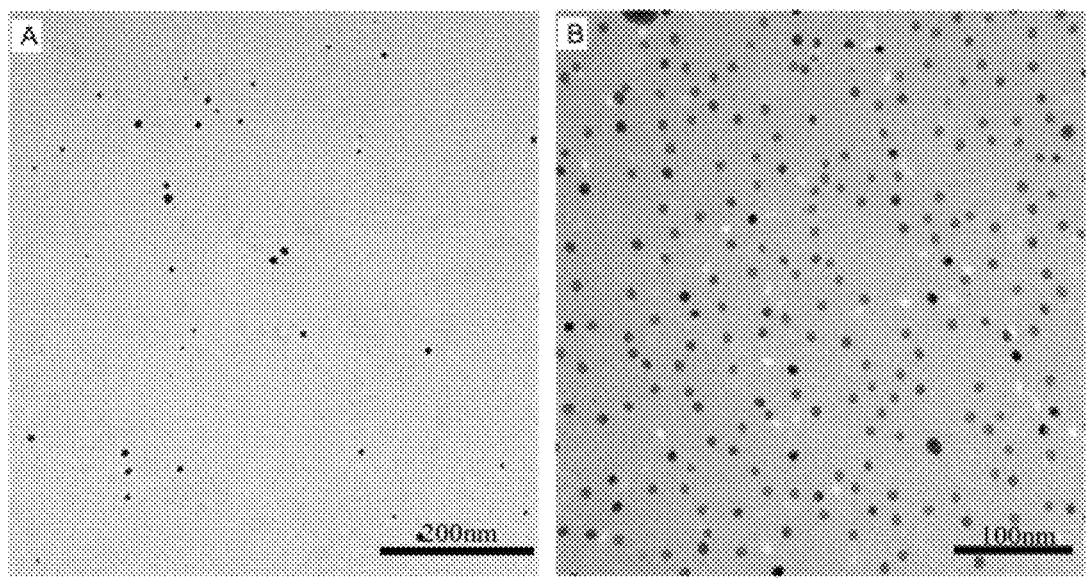
FIG. 7 shows TEM images of PEG-conjugated AuNPs, which were removed from (a) $SiO_2$-1N-AuNPs, and (b) $SiO_2$-3N-AuNPs by reacting with 3.6 mM of $PEG_{5000}$-SH at pH 9.0.
Figure 8:
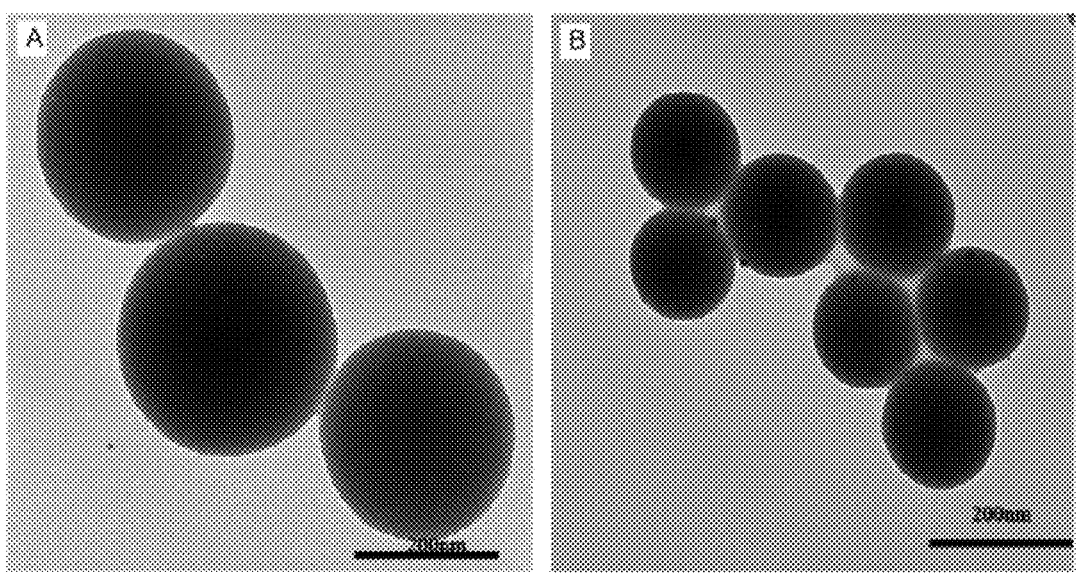
FIG. 8 shows TEM images of (a) $SiO_2$-1N-AuNPs and (b) $SiO_2$-3N-AuNPs samples after AuNPs were removed from the surface of the solid silica template.

FT-IR spectroscopy was employed to characterize the functional group on the surfaces of PEG-modified AuNPs (FIG. 3A). The specific peaks from stretching of the PEG molecule were assigned as follows: C—O—C: 1103 cm$^{-1}$, C—H: 2916 cm$^{-1}$ and —OH: 3434 cm$^{-1}$. By observing characteristic vibration bands of PEG molecules that have replaced Silica-1N and -3N samples, it was possible to verify that PEG molecules had indeed modified the AuNPs surfaces. The attachment of PEG$_{5000}$ on AuNP surfaces was also confirmed by thermogravimetric analyses (TGA) as shown in FIG. 3B. The decomposition of AuNPs-PEG$_{5000}$ (i.e., PEG-conjugated AuNPs) samples by heating process mainly came from the loss of adsorbed H$_2$O and the combustion of the PEG organic ligand. When the temperature was raised above 280° C., the weight loss was significant due to the degradation of the PEG molecules.

In FIG. 3B, the curve (a) represents the weight versus temperature relationship of naked AuNPs. The AuNPs were obtained as follows: Silica-1N-AuNPs were treated with NH$_4$F to dissolve the silica template and obtain naked AuNPs absorbed on amine groups. Upon heating to 280° C., the amine groups were melted and left AuNPs intact. The weight loss of AuNPs was only 4%. This indicated that AuNPs synthesized on the silica template were mostly naked, i.e., the AuNPs absorbed and/or immobilized onto the amine-modified SiNP were without surface modifications.

In FIG. 3B, the curve (b) represents the weight versus temperature relationship of PEG-conjugated AuNPs synthesized by PEG post-modification of citrate-reduced and protected AuNPs. The citrate-protected AuNPs were synthesized by reacting citrate with Au$^{3+}$, in which citrate is a reducing agent. At a temperature above 280° C., the weight loss of PEG-conjugated AuNPs synthesized from PEG post-modification of citrate-reduced AuNPs was 20%. This indicated that for PEG-conjugated AuNPs synthesized from citrate-reduced AuNPs, the PEG5000 shell was 20% by weight.

In FIG. 3B, the curve (c) represents the weight versus temperature relationship of PEG-conjugated AuNPs synthesized from PEG reaction with Silica-1N-AuNPs. The PEG could easily react with AuNPs immobilized onto the amine-modified SiNP and thus replaced the amine-modified silica template and formed PEG-conjugated AuNPs. At a temperature above 280° C., the weight loss of PEG-conjugated AuNPs synthesized from PEG exchange with Silica-1N-AuNPs was 73%. This indicated that for PEG-conjugated AuNPs synthesized from the AuNPs immobilized onto a monoamine-modified SiNP template, the PEG5000 shell was 73% by weight.

In FIG. 3B, the curve (d) represents the weight versus temperature relationship of PEG-conjugated AuNPs synthesized from PEG reaction with Silica-3N-AuNPs. At a temperature above 280° C., the weight loss of PEG-conjugated AuNPs synthesized from PEG exchange with Silica-3N-AuNPs was 82%. This indicated that in the PEG-conjugated AuNPs synthesized from AuNPs immobilized onto a triamine-modified SiNP template, the PEG5000 shell was 82% by weight.

The above data suggested that AuNPs synthesized on a triamine-modified SiNP template afforded a greater ligand surface density than AuNPs synthesized on a monoamine-modified SiNP template. Using the ligand PEG5000 as an example, ligand surface densities on the AuNPs surfaces were calculated as 1.26, 10.46 and 17.62 ligand molecules/nm$^2$ for PEG-conjugated AuNPs of the curves (b), (c) and (d), respectively (FIG. 3B).

As described above, ligand surface density on AuNPs was impacted by the presence or absence of a template during AuNP synthesis. The chemical and physical structures of the template for synthesizing AuNPs also impacted ligand post-modification efficiency. Table 1 shows the ligand conjugation efficiency was better in AuNPs synthesized on an amine-modified template than on an MSN template. The ligand conjugation efficiency was calculated by the weight ratio of ligand-conjugated AuNPs to the template with AuNPs absorbed and/or immobilized onto the surface thereof. The data indicated that the silica template afforded a much higher ligand conjugation efficiency (or ligand exchange/modification efficiency) than the MSN template. Here, the MSN-3N-AuNPs were synthesized by a method similar to SiO2-3N-AuNPs. The Au$^{3+}$ ions were first attached to an MSN template, usually attached to the pores of MSN, whereas in the case of silica particle template, Au$^{3+}$ ions were attached to the flat surface of the SiO2 beads. The Au$^{3+}$ ions attached to the solid MSN were then reduced by synchrotron X-ray radiation and form AuNPs absorbed/immobilized to the MSN.

AuNPs immobilized to the MSN had difficulties to be exchanged with the ligand and thus their ligand conjugation efficiency was poor compared to those immobilized onto amine-modified SiNP. In addition, the monoamine-modified silica template gave better ligand exchange efficiency than the triamine-modified silica template, which might be due to that the triamine functional group on the silica template surface had a tighter bonding with AuNPs and thus decreased the ligand exchange efficiency. A ligand of small size such as glutathione (GSH) could have as high as more than 90% ligand exchange efficiency and the ligand conjugation efficiency was concentration-dependent (Table 1).

TABLE 1

| | AuNPs absorbed/ immobilized on template | Ligand | Ligand conjugation efficiency | Ligand concentration |
|---|---|---|---|---|
| 1 | SiO$_2$—1N—AuNP | PEG | 85.9% | 3.6 mM |
| 2 | SiO$_2$—3N—AuNP | PEG | 70.09% | 3.6 mM |
| 3 | MSN-3N—AuNP | PEG | 59.3% | 3.6 mM |
| 4 | SiO$_2$—1N—AuNP | GSH | 91.6% (62.2%) | 16 mM (1.6 mM) |
| 5 | SiO$_2$—3N—AuNP | GSH | 80.8% (58.1%) | 16 mM (1.6 mM) |

Table 2 shows the cellular uptake efficiency of functionalized AuNPs. (1) PEG-conjugated AuNPs synthesized by reacting PEG with silica-1N-AuNPs failed to enter cells. The gold content in cells ($1.3 \times 10^5$ cells) was thus non-detectable. (2) TAT-conjugated AuNPs synthesized by reacting TAT with silica-1N-AuNPs were able to enter cells. (3) TAT/PEG bivalent-conjugated AuNPs synthesized by reacting TAT and PEG (bivalent ligands) with silica-1N-AuNPs were able to enter cells, in spite of the high MW PEG group. (4) Citrate-protected AuNPs were able to enter cells. The citrate-protected AuNPs were synthesized by reducing Au$^{3+}$ with NaBH4 in the presence of citrate solution. (5) TAT-conjugated AuNPs synthesized by reacting TAT with citrate-protected AuNPs had poor cellular uptake efficiency, which indicated poor conjugation efficiency between TAT and citrate-protected AuNPs. (6) TAT/PEG bivalent-conjugated AuNPs synthesized by reacting TAT and PEG (bivalent ligands) with citrate-protected AuNPs had less cellular uptake efficiency than TAT/PEG bivalent-conjugated AuNPs synthesized from silica-1N-AuNPs. The data proved that the cellular uptake efficiency of ligand-conjugated AuNPs is related to how the AuNP conjugates were synthesized and that the synthesis of bare AuNPs on a silica particle template could enhance ligand post-modification of AuNP surface.

TABLE 2

| | Ligand | Ligand* conc. (µM) | AuNP or ligand-conjugated AuNP dose (nM)** | Au content in cells*** (ng) |
|---|---|---|---|---|
| 1 | PEG | 333 | 8.57 | Non-detectable |
| 2 | TAT | 333 | 0.07 | 27.94 |
| 3 | TAT/PEG***** | 333/333 | 8.57 | 82.57 |
| 4 | Citrate | — | 8.57 (citrate-protected AuNP) | 16.15 |
| 5 | TAT | 333 | 8.57 | <4 |
| 6 | TAT/PEG***** | 333/333 | 8.57 | 20.59 |

Figure 9:
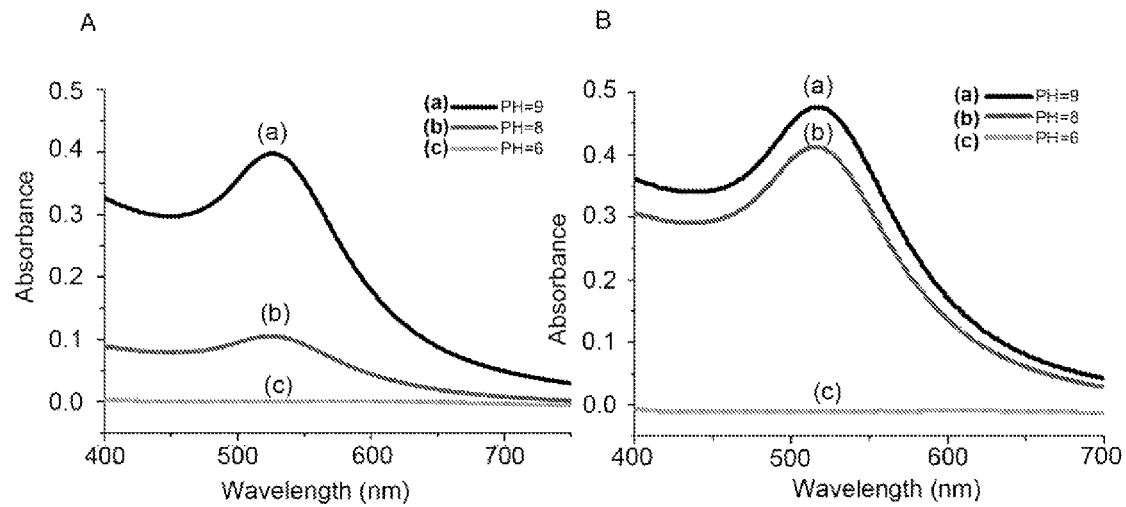
FIG. 9 shows the UV-Vis spectra of $PEG_{5000}$-modified AuNPs removed from the (A) $SiO_2$-1N-AuNPs and (B) $SiO_2$-3N-AuNPs samples at various pH values.

*Ligand conc. for exchange with AuNPs absorbed/immobilized on the silica particle template to obtain ligand-conjugated AuNPs.
**The dose of AuNPs or ligand-conjugated AuNPs for treating cells. An equal volume of culture medium containing 10% FBS was used to dilute AuNP or ligand-conjugated AuNP solution before treating cells.
***The cell number was $1.3 \times 10^5$ cells. The AuNP concentration and Au content were analyzed by ICP-MS.
*****bivalent ligands FIG. 9 shows the UV-Vis spectra of PEG$_{5000}$-modified AuNPs removed from the SiO$_2$-1N-AuNPs (FIG. 9A) and SiO$_2$-3N-AuNPs samples (FIG. 9B) at different pH values, respectively. The data showed that amounts of PEG$_{5000}$-modified AuNPs removed from the template solid phase and present in the solution phase were different at different pH values. Compared with the SiO$_2$-1N-AuNPs samples, SiO$_2$-3N-AuNPs showed removal of more amounts of AuNPs at pH 8.0. This may be explained by steric effects. The triamine (3N) functional group has a long arm that is apart from the silica surfaces and thus the AuNPs attached thereon encountered relatively low steric hindrance and were relatively easier to be released or replaced from the template at pH 8.0 by the ligand PEG.

FIG. 10 shows UV-Vis spectra of PEG-conjugated AuNPs removed from SiO$_2$-1N-AuNPs (FIG. 10A) and SiO$_2$-3N-AuNPs (FIG. 10B), respectively, with various concentrations of the ligand PEG$_{5000}$-SH (5, 3.5, 1.78, 0.9, and 0.47 mM). The images of white light absorbance indicated that the amount of AuNPs being replaced from the silica template via PEG surface modification of the AuNPs was PEG-concentration dependent.

By employing solid phase template synthetic approach, post-modification of naked AuNPs surfaces with PEG$_{5000}$-SH had high yields and high efficiency. Therefore, the TGA data of AuNPs-PEG$_{5000}$ samples, synthesized from reacting PEG$_{5000}$ with Silica-1N-AuNPs and Silica-3N-AuNPs, showed a very high weight loss of surface PEG molecules (w/w % weight loss 73% and 82%, respectively). However, naked AuNPs, which was obtained after NH$_4$F dissolution of silica template from Silica-1N-AuNPs samples, showed only 4% of weight loss after melting at the high temperature (FIG. 3B, curve (a)). The 4% weight loss was due to melting of the amine groups onto which AuNPs were absorbed. The fact that AuNPs showed very low weight loss after being heated at a high temperature confirmed that AuNPs on the SiNPs surfaces mostly exist in a naked form and therefore very few aminosilane groups bond to the surfaces of AuNPs.

In summary, the invention relates to the discovery of a simple and rapid surface modification of naked AuNPs, in which the naked AuNPs were synthesized from in situ reduction by employing a high energy of synchrotron X-ray as a reductive source to synthesize bare AuNPs onto a hard template of aminosilane modified silica NPs. The amino groups on the surfaces of silica NPs provided an appropriate distance and a site of an isolated environment, which can generate a single-site reductive environment and therefore prevent the aggregation among neighboring naked AuNPs. The reduction of AuNPs using this design has the advantage such as rapid, clean, highly efficient, environmentally friendly, low cytotoxicity (minimal Au$^{3+}$ residues) and room temperature synthesis. In addition, the production of naked AuNPs on the surfaces of amine-modified SiNPs can efficiently prevent aggregations of SiNPs and AuNPs. These two different nanoparticles can suspend well in different buffer at pH 7.0. The extra stability of naked AuNPs on Silica surface may be attributed to the strong electrostatic repulsion from reduced Silica-AuNPs samples. Through the help of a strong electrostatic repulsion among different Silica-NPs, the naked AuNPs can keep a suitable distance from each other to prevent aggregation caused by the high affinity of naked NPs surfaces. Therefore, an organic ligand which expects to modify the AuNP surface can easily and rapidly replace the amino-modified silica through introduction of a thiol-containing organic molecule. The removal (release) of AuNPs from the silica template was also synchronously finished via a one-step exchange of AuNP-aminosilane bond with a PEG-thiol molecule.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention

What is claimed is:

1. A method of synthesizing ligand-conjugated gold nanoparticles (AuNPs), comprising:
   providing amine-modified silica particles;
   providing a solution comprising $HAuCl_4$;
   suspending the amine-modified silica particles in the solution comprising the $HAuCl_4$;
   producing silica particles-$NH_3^+AuCl_4^-$ complexes by allowing $Au^{3+}$ ions in the solution to be adsorbed and/or immobilized onto the surface of the amine-modified silica particles, wherein the solution has no mesoporous silica nanoparticles (MSN) present;
   exposing the silica particles-$NH_3^+AuCl_4^-$ complexes to radiation to reduce the $Au^{3+}$ ions and obtain bare gold nanoparticles (AuNPs) adsorbed and/or immobilized onto the surface of the amine-modified silica particles, wherein the bare AuNPs are without organic surface modifications; and
   reacting a ligand with the bare AuNPs adsorbed and/or immobilized onto the surface of the amine-modified silica particles under sonication to desorb and modify the bare AuNPs and thereby synthesizing the ligand-conjugated gold nanoparticles.

2. The method of claim 1, wherein prior to providing the amine-modified silica particle, the method further comprises:
   reacting an aminosilane with silica nanoparticles to obtain the amine-modified silica particle.

3. The method of claim 2, wherein amionosilane is at least one selected from the group consisting of 3-aminopropyltrimethoxysilane- or N-[3-(trimethoxylsiliyl)-propyl]diethylene-triamine.

4. The method of claim 1, wherein the ligand comprises a functional group selected from the group consisting of a thiol, an amine and phosphine groups.

5. The method of claim 1, wherein the ligand comprises at least one polymer selected from the group consisting of a synthetic polymer and a biopolymer.

6. The method of claim 1, wherein the ligand is at least one selected from the group consisting of polyethylene glycol (PEG), PEG derivatives, TAT (SEQ ID NO: 1) and glutathione (GSH), a polynucleotide and a protein.

7. The method of claim 1, wherein the radiation is selected from the group consisting of X-rays, microwaves, gamma-rays and neutrons.

8. The method of claim 1, wherein the $Au^{3+}$ ions immobilized onto the surface of the amine-modified silica particle are exposed to synchrotron X-ray.

9. The method of claim 1, further comprising:
   performing centrifugation to pellet the amine-modified silica particles; and
   collecting the ligand-conjugated AuNPs in supernatant.

10. The method of claim 1, wherein the ligand-reacting step is performed at a pH of greater than 6.

11. The method of claim 1, wherein the ligand-reacting step is performed under a condition that permits the ligand to carry a negative charge.

12. A method of synthesizing ligand-conjugated gold nanoparticles (AuNPs) comprising:
   providing a solution comprising amine-modified silica particles with bare gold nanoparticles (AuNPs) adsorbed and/or immobilized onto the surface thereof, wherein the bare AuNPs are without organic surface modifications and the solution has no mesoporous silica nanoparticles (MSN) present; and
   releasing the bare AuNPs from the amine-modified silica particles through surface modification of the bare AuNPs by reacting a ligand with the bare AuNPs adsorbed and/or immobilized onto the surface of the amine-modified silica particle in the solution and thereby synthesizing the ligand-conjugated AuNPs wherein the releasing step is carried out by performing sonication of the solution.

13. The method of claim 12, further comprising:
   performing centrifugation to pellet the amine-modified silica particles; and
   collecting the ligand-conjugated AuNPs in supernatant.

14. The method of claim 12, wherein the ligand comprises a functional group selected from the group consisting of a thiol, an amine and phosphine groups.

15. The method of claim 12, wherein the ligand comprises at least one polymer chosen from a synthetic polymer and a biopolymer.

16. The method of claim 1, wherein the radiation-exposing step is performed in the absence of an organic ligand and the ligand-reacting step is performed in the absence of a chemical catalyst.

17. The method of claim 1, wherein prior to the exposing step further comprises:
   collecting the silica particles-$NH_3^+AuCl_4^-$ complexes by centrifugation; and
   resuspending the silica particles-$NH_3^+AuCl_4^-$ complexes in $H_2O$.

18. The method of claim 1, wherein the exposing step comprises exposing the silica particles-$NH_3^+AuCl_4^-$ complexes to X-rays.

* * * * *